(12) United States Patent
Tan et al.

(10) Patent No.: US 10,874,601 B2
(45) Date of Patent: *Dec. 29, 2020

(54) COMPOSITIONS AND METHODS FOR TREATING HAIR

(71) Applicant: L'OREAL, Paris (FR)

(72) Inventors: Siliu Tan, Westfield, NJ (US); Nghi Van Nguyen, Edison, NJ (US); Jim Singer, South Orange, NJ (US); Jean-Thierry Simonnet, Mamaroneck, NY (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/852,130

(22) Filed: Dec. 22, 2017

(65) Prior Publication Data

US 2018/0185262 A1 Jul. 5, 2018

Related U.S. Application Data

(63) Continuation of application No. 13/931,222, filed on Jun. 28, 2013, now Pat. No. 9,884,002.

(51) Int. Cl.
*A61Q 5/06* (2006.01)
*A61K 8/81* (2006.01)
*A45D 7/06* (2006.01)
*A45D 7/00* (2006.01)

(52) U.S. Cl.
CPC ............. *A61K 8/8147* (2013.01); *A45D 7/06* (2013.01); *A61K 8/8152* (2013.01); *A61Q 5/06* (2013.01); *A45D 2007/002* (2013.01); *A61K 2800/594* (2013.01)

(58) Field of Classification Search
None
See application file for complete search history.

(56) References Cited

U.S. PATENT DOCUMENTS

| | | |
|---|---|---|
| 3,110,695 A | 11/1963 | Ceresa |
| 3,304,273 A | 2/1967 | Stamberger |
| 3,383,351 A | 5/1968 | Stamberger |
| 3,412,054 A | 11/1968 | Milligan et al. |
| 3,523,095 A | 8/1970 | Laurito et al. |
| 3,915,921 A | 10/1975 | Schlatzer, Jr. |
| 4,003,699 A | 1/1977 | Rose et al. |
| RE30,199 E | 1/1980 | Rose et al. |
| 4,509,949 A | 4/1985 | Huang et al. |
| 4,644,030 A | 2/1987 | Loewrigkeit et al. |
| 4,710,374 A | 12/1987 | Grollier et al. |
| 4,798,721 A | 1/1989 | Yahagi et al. |
| 4,963,348 A | 10/1990 | Bolich, Jr. et al. |
| 4,985,239 A | 1/1991 | Yahagi et al. |
| 5,061,289 A | 10/1991 | Clausen et al. |
| 5,085,859 A | 2/1992 | Halloran et al. |
| 5,156,911 A | 10/1992 | Stewart |
| 5,173,526 A | 12/1992 | Vijayendran et al. |
| 5,221,534 A | 6/1993 | DesLauriers et al. |
| 5,380,340 A | 1/1995 | Neunhoeffer et al. |
| 5,441,728 A | 8/1995 | Tsaur et al. |
| 5,534,267 A | 7/1996 | Neunhoeffer et al. |
| 5,565,216 A | 10/1996 | Cowsar et al. |
| 5,618,523 A | 4/1997 | Zysman et al. |
| 5,637,291 A | 6/1997 | Bara et al. |
| 5,663,366 A | 9/1997 | Neunhoeffer et al. |
| 5,679,327 A | 10/1997 | Darkwa et al. |
| 5,708,151 A | 1/1998 | Mockli |
| 5,753,215 A | 5/1998 | Mougin et al. |
| 5,766,576 A | 6/1998 | Lowe et al. |
| 5,911,973 A | 6/1999 | de la Poterie |
| 5,932,194 A | 8/1999 | Plessix et al. |
| 6,013,682 A | 1/2000 | Dalle et al. |
| 6,099,592 A | 8/2000 | Vidal et al. |
| 6,110,451 A | 8/2000 | Matz et al. |
| 6,120,778 A | 9/2000 | Simonnet |
| 6,126,929 A | 10/2000 | Mougin |
| 6,126,948 A | 10/2000 | Simonnet et al. |
| 6,165,446 A | 12/2000 | Samain et al. |
| 6,214,328 B1 | 4/2001 | Chang et al. |
| 6,268,431 B1 | 7/2001 | Snyder et al. |
| 6,284,003 B1 | 9/2001 | Rose et al. |
| 6,338,741 B1 | 1/2002 | Vidal et al. |
| 6,399,050 B1 | 6/2002 | Pasquet et al. |
| 6,432,385 B1 | 8/2002 | Rollat-Corvol et al. |
| 6,464,990 B2 | 10/2002 | Simonnet et al. |
| 6,482,394 B1 * | 11/2002 | Schehlmann .......... A61K 8/046 424/47 |

(Continued)

FOREIGN PATENT DOCUMENTS

| | | |
|---|---|---|
| DE | 1152536 B | 8/1963 |
| DE | 2359399 A1 | 6/1975 |

(Continued)

OTHER PUBLICATIONS

Communication Pursuant to Article 94(3) EPC for counterpart Application No. 14818457.4-1114, dated Mar. 12, 2018.
Non-Final Office Action for U.S. Appl. No. 13/931,187, dated Feb. 13, 2015.
Final Office Action for U.S. Appl. No. 13/931,187, dated Jul. 20, 2015.
Non-Final Office Action for U.S. Appl. No. 13/931,187, dated Mar. 29, 2016.
Final Office Action for U.S. Appl. No. 13/931,187, dated Aug. 8, 2016.
Non-Final Office Action for U.S. Appl. No. 13/931,187, dated Feb. 27, 2017.
Notice of Allowance for U.S. Appl. No. 13/931,187, dated Sep. 28, 2017.
Supplemental Notice of Allowance for U.S. Appl. No. 13/931,187, dated Oct. 12, 2017.

(Continued)

*Primary Examiner* — Jyothsna A Venkat
(74) *Attorney, Agent, or Firm* — The Marbury Law Group, PLLC

(57) ABSTRACT

Disclosed are hair styling compositions comprising at least two latex acrylate polymers, wherein at least one latex acrylate polymer is a film-forming polymer. Methods of styling the hair are also disclosed.

19 Claims, No Drawings

(56) References Cited

U.S. PATENT DOCUMENTS

| | | | |
|---|---|---|---|
| 6,491,932 B1 | 12/2002 | Ramin et al. | |
| 6,585,965 B1 | 7/2003 | Carballada et al. | |
| 6,592,633 B2 | 7/2003 | Lang et al. | |
| 6,613,315 B1 | 9/2003 | Dupuis | |
| 6,645,258 B2 | 11/2003 | Vidal et al. | |
| 6,703,028 B1 | 3/2004 | Samain et al. | |
| 6,726,916 B1 | 4/2004 | Ramin | |
| 6,730,789 B1 | 5/2004 | Birault et al. | |
| 6,749,837 B1 | 6/2004 | Samain et al. | |
| 6,805,136 B2 * | 10/2004 | Browning | A45D 7/06 132/204 |
| 6,946,123 B2 | 9/2005 | De La Poterie et al. | |
| 7,211,244 B2 | 5/2007 | Auguste et al. | |
| 7,378,085 B2 | 5/2008 | Belli | |
| 7,651,693 B2 | 1/2010 | Merlau et al. | |
| 7,740,832 B1 | 6/2010 | Rollat-Corvol et al. | |
| 7,785,613 B2 | 8/2010 | Collin et al. | |
| 7,993,632 B2 | 8/2011 | Jager Lezer et al. | |
| 8,343,238 B1 | 1/2013 | Lopez et al. | |
| 8,398,961 B2 | 3/2013 | Kaplan et al. | |
| 8,691,200 B2 | 4/2014 | Vilbert | |
| 8,865,147 B2 | 10/2014 | Rizk et al. | |
| 9,072,686 B2 | 7/2015 | Bui et al. | |
| 9,402,800 B2 | 8/2016 | Li et al. | |
| 9,801,808 B2 * | 10/2017 | Tan | A61K 8/04 |
| 9,814,668 B2 * | 11/2017 | Tan | A61K 8/044 |
| 9,814,669 B2 * | 11/2017 | Shin | A61K 8/895 |
| 9,884,002 B2 * | 2/2018 | Tan | A61K 8/8147 |
| 9,884,003 B2 * | 2/2018 | Tan | A61K 8/8147 |
| 9,884,004 B2 * | 2/2018 | Tan | A61K 8/87 |
| 2002/0007521 A1 | 1/2002 | Lang et al. | |
| 2002/0010970 A1 | 1/2002 | Collard et al. | |
| 2002/0022009 A1 | 2/2002 | De La Poterie et al. | |
| 2002/0050013 A1 | 5/2002 | Vidal et al. | |
| 2002/0055562 A1 | 5/2002 | Butuc | |
| 2002/0061320 A1 | 5/2002 | Belli | |
| 2002/0198328 A1 | 12/2002 | L'Alloret | |
| 2003/0019051 A9 | 1/2003 | Vidal et al. | |
| 2003/0026815 A1 | 2/2003 | Scott et al. | |
| 2003/0044440 A1 | 3/2003 | Toumi | |
| 2003/0053976 A1 | 3/2003 | Tournilhac et al. | |
| 2003/0059377 A1 | 3/2003 | Riley | |
| 2003/0059388 A1 | 3/2003 | Auguste et al. | |
| 2003/0064045 A1 | 4/2003 | Tournilhac et al. | |
| 2003/0103927 A1 | 6/2003 | Maubru | |
| 2003/0138465 A9 | 7/2003 | Douin et al. | |
| 2003/0147832 A1 | 8/2003 | L'Alloret | |
| 2003/0147834 A1 | 8/2003 | Rollat et al. | |
| 2003/0161804 A1 | 8/2003 | Perron et al. | |
| 2004/0071646 A1 | 4/2004 | Pataut et al. | |
| 2004/0096474 A1 | 5/2004 | Merlau et al. | |
| 2004/0214913 A1 | 10/2004 | L'Alloret | |
| 2005/0008605 A1 | 1/2005 | L'Alloret | |
| 2005/0020779 A1 | 1/2005 | Mougin et al. | |
| 2005/0025736 A1 | 2/2005 | Jachowicz et al. | |
| 2005/0048016 A1 | 3/2005 | Lebreton et al. | |
| 2005/0053568 A1 | 3/2005 | Aubrun-Sonneville et al. | |
| 2005/0065253 A1 | 3/2005 | Collin et al. | |
| 2005/0089490 A1 | 4/2005 | Jachowicz et al. | |
| 2005/0220723 A1 | 10/2005 | Benabdillah et al. | |
| 2006/0051311 A1 | 3/2006 | Walter et al. | |
| 2006/0115446 A1 | 6/2006 | Rollat-Corvol et al. | |
| 2006/0134043 A1 | 6/2006 | Nakamura | |
| 2006/0182702 A1 | 8/2006 | Lazzeri et al. | |
| 2006/0292095 A1 | 12/2006 | Biatry et al. | |
| 2007/0031361 A1 | 2/2007 | Herrmann et al. | |
| 2007/0190008 A1 | 8/2007 | Campain et al. | |
| 2007/0196383 A1 | 8/2007 | Murakami et al. | |
| 2007/0224140 A1 | 9/2007 | Quadir et al. | |
| 2007/0286833 A1 | 12/2007 | Keller et al. | |
| 2008/0138307 A1 | 6/2008 | Bazemore et al. | |
| 2008/0175808 A1 | 7/2008 | Pavel | |
| 2008/0305064 A1 | 12/2008 | Bui et al. | |
| 2009/0035335 A1 | 2/2009 | Marotta et al. | |
| 2009/0060858 A1 | 3/2009 | Schwarzwaelder et al. | |
| 2009/0074695 A1 | 3/2009 | Mahe et al. | |
| 2009/0280076 A1 | 11/2009 | Yoshida et al. | |
| 2009/0297467 A1 | 12/2009 | Laurent et al. | |
| 2009/0317432 A1 | 12/2009 | Kergosien | |
| 2010/0028284 A1 | 2/2010 | Atis et al. | |
| 2010/0119467 A1 | 5/2010 | Dumousseaux et al. | |
| 2010/0189678 A1 * | 7/2010 | Knappe | A61K 8/8152 424/70.16 |
| 2010/0278770 A1 | 11/2010 | Arditty et al. | |
| 2011/0014139 A1 | 1/2011 | Viala et al. | |
| 2011/0015279 A1 | 1/2011 | Doerr et al. | |
| 2011/0044925 A1 * | 2/2011 | Pye | A61K 8/60 424/70.11 |
| 2011/0097289 A1 | 4/2011 | Viala et al. | |
| 2011/0097293 A1 | 4/2011 | Grey et al. | |
| 2011/0142780 A1 | 6/2011 | Hentrich et al. | |
| 2011/0150802 A1 | 6/2011 | Bui et al. | |
| 2011/0150807 A1 | 6/2011 | Bui et al. | |
| 2012/0247500 A1 | 10/2012 | Plos et al. | |
| 2012/0282309 A1 | 11/2012 | Dihora et al. | |
| 2012/0308496 A1 | 12/2012 | Viala et al. | |
| 2013/0039874 A1 | 2/2013 | Li et al. | |
| 2013/0068243 A1 | 3/2013 | Birkel et al. | |
| 2013/0068849 A1 | 3/2013 | Birkel et al. | |
| 2013/0084256 A1 | 4/2013 | Li et al. | |
| 2013/0167863 A1 | 7/2013 | Schmelz et al. | |
| 2013/0171084 A1 | 7/2013 | Kawaratani et al. | |
| 2013/0284198 A1 | 10/2013 | Rizk et al. | |
| 2014/0102468 A1 | 4/2014 | Piston et al. | |
| 2014/0105845 A1 | 4/2014 | Bui et al. | |
| 2014/0105945 A1 | 4/2014 | Bui et al. | |
| 2014/0186270 A1 | 7/2014 | Suleiman et al. | |
| 2014/0328780 A1 | 11/2014 | Li et al. | |
| 2015/0004116 A1 | 1/2015 | Tan et al. | |
| 2015/0004119 A1 | 1/2015 | Tan et al. | |
| 2015/0004120 A1 | 1/2015 | Tan et al. | |
| 2015/0004121 A1 | 1/2015 | Tan et al. | |

FOREIGN PATENT DOCUMENTS

| | | |
|---|---|---|
| DE | 2364398 A1 | 10/1975 |
| DE | 3843892 A1 | 6/1990 |
| DE | 4133957 A1 | 4/1993 |
| DE | 19543988 A1 | 5/1997 |
| DE | 102008038104 A1 | 2/2010 |
| DE | 102009054516 A1 | 6/2011 |
| EP | 0216479 A1 | 4/1987 |
| EP | 0898958 A1 | 3/1993 |
| EP | 0898960 A1 | 3/1993 |
| EP | 0692237 A1 | 1/1996 |
| EP | 0714954 A2 | 6/1996 |
| EP | 0770375 A1 | 5/1997 |
| EP | 0847752 A1 | 6/1998 |
| EP | 0874017 A2 | 10/1998 |
| EP | 1082953 A1 | 3/2001 |
| EP | 1291051 A2 | 3/2003 |
| EP | 1466588 A1 | 10/2004 |
| EP | 1652509 A2 | 5/2006 |
| EP | 2161016 A1 | 3/2010 |
| EP | 2356981 A1 | 8/2011 |
| EP | 2570110 A2 | 3/2013 |
| EP | 2570192 A1 | 3/2013 |
| FR | 2633940 A1 | 1/1991 |
| FR | 2733749 A1 | 11/1996 |
| FR | 2774899 A1 | 8/1999 |
| FR | 2801308 A1 | 5/2001 |
| FR | 2834458 A1 | 7/2003 |
| FR | 2856923 A1 | 1/2005 |
| FR | 2889943 A1 | 3/2007 |
| FR | 2898050 A1 | 9/2007 |
| FR | 2961103 A1 | 12/2011 |
| FR | 2968978 A1 | 6/2012 |
| GB | 1026978 A | 4/1966 |
| GB | 1040452 A | 8/1966 |
| GB | 1153196 A | 5/1969 |
| JP | 02-019576 A | 1/1990 |
| JP | 05-163124 A | 6/1993 |
| JP | H07-207102 A | 8/1995 |
| JP | H07-048231 A | 9/1996 |

(56) References Cited

FOREIGN PATENT DOCUMENTS

| | | | |
|---|---|---|---|
| JP | H09-194337 | A | 7/1997 |
| JP | S62-063508 | A | 9/1998 |
| JP | 2001-089324 | A | 4/2001 |
| JP | 2001-151646 | A | 6/2001 |
| JP | 2002-501481 | A | 1/2002 |
| JP | 2002-145728 | A | 5/2002 |
| JP | 2004-505902 | A | 2/2004 |
| JP | 2004-168776 | A | 6/2004 |
| JP | 2004-532879 | A | 10/2004 |
| JP | 2005-510598 | A | 4/2005 |
| JP | 2006-070030 | A | 3/2006 |
| JP | 2007-217314 | A | 8/2007 |
| JP | 2007-254459 | A | 10/2007 |
| JP | 2009-040755 | A | 2/2009 |
| JP | 2009-286750 | A | 12/2009 |
| JP | 2011-126884 | A | 6/2011 |
| JP | 2014-526376 | A | 10/2014 |
| JP | 2014-528420 | A | 10/2014 |
| KR | 10-2010-015168 | A | 9/2010 |
| RU | 2001123246 | A | 6/2003 |
| RU | 2219900 | C2 | 12/2003 |
| RU | 2183449 | C2 | 3/2004 |
| RU | 2009120397 | A | 12/2010 |
| WO | 94/08970 | A1 | 4/1994 |
| WO | 94/085369 | A1 | 4/1994 |
| WO | 95/01772 | A1 | 1/1995 |
| WO | 95/15144 | A1 | 6/1995 |
| WO | 96/15765 | A1 | 5/1996 |
| WO | 98/31329 | A1 | 7/1998 |
| WO | 01/19333 | A1 | 3/2001 |
| WO | 01/35910 | A1 | 5/2001 |
| WO | 2005/100444 | A1 | 10/2005 |
| WO | 2007/099269 | A2 | 9/2007 |
| WO | 2007/102972 | A1 | 9/2007 |
| WO | 2010/133658 | A2 | 11/2010 |
| WO | 2011/056332 | A1 | 5/2011 |
| WO | 2011/069786 | A2 | 6/2011 |
| WO | 2011/137338 | A2 | 11/2011 |
| WO | 2012/049146 | A2 | 4/2012 |
| WO | 2012/072774 | A1 | 6/2012 |
| WO | 2013/059106 | A1 | 4/2013 |
| WO | 2013/074210 | A1 | 5/2013 |
| WO | 2013/092378 | A1 | 6/2013 |
| WO | 2013/092379 | A1 | 6/2013 |
| WO | 2013/092380 | A1 | 6/2013 |
| WO | 2013/092381 | A1 | 6/2013 |
| WO | 2013/092382 | A1 | 6/2013 |
| WO | 2013/092562 | A1 | 6/2013 |
| WO | 2013/092779 | A2 | 6/2013 |
| WO | 2013/092788 | A1 | 6/2013 |
| WO | 2014/001390 | A1 | 1/2014 |
| WO | 2014/001391 | A1 | 1/2014 |
| WO | 2014/058856 | A1 | 4/2014 |
| WO | 2014/062334 | A1 | 4/2014 |
| WO | 2014/071354 | A1 | 5/2014 |
| WO | 2014/124066 | A1 | 8/2014 |

OTHER PUBLICATIONS

Non-Final Office Action for U.S. Appl. No. 13/931,204, dated Feb. 20, 2015.
Final Office Action for U.S. Appl. No. 13/931,204, dated Aug. 10, 2015.
Notice of Non-Compliant Response for U.S. Appl. No. 13/931,204, dated Apr. 18, 2016.
Non-Final Office Action for U.S. Appl. No. 13/931,204, dated Aug. 1, 2016.
Final Office Action for U.S. Appl. No. 13/931,204, dated Feb. 7, 2017.
Notice of Allowance for U.S. Appl. No. 13/931,204, dated Jun. 9, 2017.
Non-Final Office Action for U.S. Appl. No. 13/931,222, dated Apr. 7, 2015.
Final Office Action for U.S. Appl. No. 13/931,222, dated Jul. 28, 2015.
Non-Final Office Action for U.S. Appl. No. 13/931,222, dated Jan. 4, 2016.
Final Office Action for U.S. Appl. No. 13/931,222, dated Apr. 21, 2016.
Non-Final Office Action for U.S. Appl. No. 13/931,222, dated Feb. 27, 2017.
Notice of Allowance for U.S. Appl. No. 13/931,222, dated Sep. 25, 2017.
Non-Final Office Action for U.S. Appl. No. 13/931,238, dated Feb. 13, 2015.
Final Office Action for U.S. Appl. No. 13/931,238, dated Aug. 10, 2015.
Notice of Non-Compliant Response for U.S. Appl. No. 13/931,238, dated Apr. 18, 2016.
Non-Final Office Action for U.S. Appl. No. 13/931,238, dated Oct. 13, 2016.
Notice of Allowance for U.S. Appl. No. 13/931,238, dated Aug. 7, 2017.
Non-Final Office Action for U.S. Appl. No. 13/931,238, dated Feb. 20, 2015.
Final Office Action for U.S. Appl. No. 13/931,238, dated Aug. 11, 2015.
Non-Final Office Action for U.S. Appl. No. 13/931,238, dated Oct. 17, 2016.
Final Office Action for U.S. Appl. No. 13/931,238, dated Jul. 27, 2017.
Non-Final Office Action for U.S. Appl. No. 13/931,238, dated Feb. 8, 2018.
Non-Final Office Action for U.S. Appl. No. 13/931,260, dated Feb. 20, 2015.
Final Office Action for U.S. Appl. No. 13/931,260, dated Aug. 11, 2015.
Notice of Non-Compliant Response for U.S. Appl. No. 13/931,260, dated Apr. 15, 2016.
Non-Final Office Action for U.S. Appl. No. 13/931,260, dated Jul. 28, 2016.
Final Office Action for U.S. Appl. No. 13/931,260, dated Feb. 7, 2017.
Notice of Allowance for U.S. Appl. No. 13/931,260, dated Jun. 9, 2017.
Non-Final Office Action for U.S. Appl. No. 13/931,276, dated Feb. 17, 2015.
Final Office Action for U.S. Appl. No. 13/931,276, dated Aug. 10, 2015.
Notice of Non-Compliant Response for U.S. Appl. No. 13/931,276, dated Apr. 15, 2016.
Non-Final Office Action for U.S. Appl. No. 13/931,276, dated Oct. 6, 2016.
Notice of Allowance for U.S. Appl. No. 13/931,276, dated Jun. 19, 2017.
Non-Final Office Action for U.S. Appl. No. 13/931,288, dated Feb. 18, 2015.
Final Office Action for U.S. Appl. No. 13/931,288, dated Aug. 6, 2015.
Non-Final Office Action for U.S. Appl. No. 13/931,288, dated Apr. 22, 2016.
Final Office Action for U.S. Appl. No. 13/931,288, dated Dec. 21, 2016.
Notice of Allowance for U.S. Appl. No. 13/931,288, dated Jun. 22, 2017.
Non-Final Office Action for U.S. Appl. No. 13/931,298, dated Feb. 20, 2015.
Final Office Action for U.S. Appl. No. 13/931,298, dated Aug. 11, 2015.
Notice of Non-Compliant Response for U.S. Appl. No. 13/931,298, dated Apr. 18, 2016.
Non-Final Office Action for U.S. Appl. No. 13/931,298, dated Jul. 28, 2016.
Final Office Action for U.S. Appl. No. 13/931,298, dated Feb. 10, 2017.

(56) References Cited

OTHER PUBLICATIONS

Notice of Allowance for U.S. Appl. No. 13/931,298, dated Jul. 13, 2017.
Non-Final Office Action for U.S. Appl. No. 13/931,312, dated Feb. 18, 2015.
Final Office Action for U.S. Appl. No. 13/931,312, dated Aug. 10, 2015.
Non-Final Office Action for U.S. Appl. No. 13/931,312, dated Apr. 13, 2016.
Final Office Action for U.S. Appl. No. 13/931,312, dated Aug. 4, 2016.
Non-Final Office Action for U.S. Appl. No. 13/931,312, dated Feb. 27, 2017.
Notice of Allowance for U.S. Appl. No. 13/931,312, dated Sep. 28, 2017.
Non-Final Office Action for U.S. Appl. No. 13/931,329, dated Feb. 13, 2015.
Final Office Action for U.S. Appl. No. 13/931,329, dated Aug. 11, 2015.
Notice of Non-Compliant Response for U.S. Appl. No. 13/931,329, dated Apr. 18, 2016.
Non-Final Office Action for U.S. Appl. No. 13/931,329, dated Oct. 6, 2016.
Notice of Allowance for U.S. Appl. No. 13/931,329, dated Jun. 16, 2017.
Supplemental Notice of Allowance for U.S. Appl. No. 13/931,329, dated Jul. 11, 2017.
Non-Final Office Action for U.S. Appl. No. 14/586,105, dated Feb. 25, 2016.
Final Office Action for U.S. Appl. No. 14/586,105, dated Jul. 28, 2016.
Non-Final Office Action for U.S. Appl. No. 14/586,105, dated Apr. 7, 2017.
Final Office Action for U.S. Appl. No. 14/586,105, dated Dec. 28, 2017.
Non-Final Office Action for U.S. Appl. No. 14/578,074, dated Feb. 25, 2016.
Final Office Action for U.S. Appl. No. 14/578,074, dated Aug. 4, 2016.
Non-Final Office Action for U.S. Appl. No. 14/578,074, dated Apr. 7, 2017.
Final Office Action for U.S. Appl. No. 14/578,074, dated Dec. 22, 2017.
Non-Final Office Action for U.S. Appl. No. 14/576,639, dated Feb. 26, 2016.
Final Office Action for U.S. Appl. No. 14/576,639, dated Nov. 2, 2016.
Notice of Allowance for U.S. Appl. No. 14/576,639, dated Jul. 5, 2017.
Supplemental Notice of Allowance for U.S. Appl. No. 14/576,639, dated Jul. 17, 2017.
Non-Final Office Action for U.S. Appl. No. 14/577,579, dated Feb. 26, 2016.
Final Office Action for U.S. Appl. No. 14/577,579, dated Nov. 2, 2016.
Notice of Allowance for U.S. Appl. No. 14/577,579, dated Jun. 29, 2017.
Non-Final Office Action for U.S. Appl. No. 14/577,809, dated Jul. 10, 2015.
Final Office Action for U.S. Appl. No. 14/577,809, dated Dec. 24, 2015.
Non-Final Office Action for U.S. Appl. No. 14/577,809, dated Oct. 3, 2016.
Notice of Allowance for U.S. Appl. No. 14/577,809, dated May 10, 2017.
Non-Final Office Action for U.S. Appl. No. 14/577,740, dated Oct. 3, 2016.
Notice of Allowance for U.S. Appl. No. 14/577,740, dated Jul. 6, 2017.
Supplemental Notice of Allowance for U.S. Appl. No. 14/577,740, dated Jul. 25, 2017.
Non-Final Office Action for U.S. Appl. No. 14/578,122, dated Apr. 6, 2017.
Final Office Action for U.S. Appl. No. 14/578,122, dated Nov. 16, 2017.
English Translation of the Office Action for Counterpart Chinese Application No. 2014800480187, dated Jan. 10, 2018.
Translation of Second Chinese Office Action for counterpart Application No. 201480047973.9, dated Jul. 23, 2018.
Translation of Second Chinese Office Action for counterpart Application No. 201480048018.7, dated Jul. 23, 2018.
Extended European Search Report for counterpart EP Application No. 14817786.8, dated Oct. 14, 2016.
International Search Report and Written Opinion for copending application No. PCT/US2015/066818, dated Feb. 26, 2016.
English language abstract for EP 0898960 (Mar. 3, 1999).
English language abstract for EP 1082953 (Mar. 14, 2001).
English language abstract for FR 2633940 (Jul. 12, 1991).
English language abstract for FR 2834458 (Jul. 11, 2003).
English language abstract for FR 2898050 (Sep. 7, 2007).
English language abstract for FR 2968978 (Jun. 22, 2012).
Galgoci, Ernest C., et al., "Solvent-Free Urethane-Acrylic Hybrid Polymers for Coatings," JCT Coatings Tech, 2 (13), Feb. 2005, pp. 28-36.
Jachowicz, J., et al., "Mechanical Analysis of Elasticity and Flexibility of Virgin and Polymer-Treated Hair fiber Assemblies," J. Cosmet. Sci., 53, Nov./Dec. 2002, pp. 345-361.
Co-pending U.S. Appl. No. 13/931,187; Siliu Tan et al.,"Compositions and Methods for Treating Hair," filed Jun. 28, 2013.
Co-pending U.S. Appl. No. 13/931,204; Siliu Tan et al.,"Compositions and Methods for Treating Hair," filed Jun. 28, 2013 (now U.S. Pat. No. 9,795,555).
Co-pending U.S. Appl. No. 13/931,238; Siliu Tan et al.,"Compositions and Methods for Treating Hair," filed Jun. 28, 2013 (now U.S. Pat. No. 9,839,600).
Co-pending U.S. Appl. No. 13/931,248; Siliu Tan et al.,"Compositions and Methods for Treating Hair," filed Jun. 28, 2013.
Co-pending U.S. Appl. No. 13/931,260; Siliu Tan et al.,"Compositions and Methods for Treating Hair," filed Jun. 28, 2013 (now U.S. Pat. No. 9,789,050).
Co-pending U.S. Appl. No. 13/931,276; Siliu Tan et al.,"Compositions and Methods for Treating Hair," filed Jun. 28, 2013 (now U.S. Pat. No. 9,789,051).
Co-pending U.S. Appl. No. 13/931,288; Siliu Tan et al.,"Compositions and Methods for Treating Hair," filed Jun. 28, 2013 (now U.S. Pat. No. 9,788,627).
Co-pending U.S. Appl. No. 13/931,298; Siliu Tan et al.,"Compositions and Methods for Treating Hair," filed Jun. 28, 2013 (now U.S. Pat. No. 9,801,804).
Co-pending U.S. Appl. No. 13/931,312; Siliu Tan et al.,"Compositions and Methods for Treating Hair," filed Jun. 28, 2013.
Co-pending U.S. Appl. No. 13/931,329; Siliu Tan et al.,"Compositions and Methods for Treating Hair," filed Jun. 28, 2013 (now U.S. Pat. No. 9,795,556).
International Search Report and Written Opinion for counterpart Application PCT/US2015/065967, dated Jul. 5, 2016.
International Search Report and Written Opinion for counterpart Application PCT/US2015/065975, dated Jul. 5, 2016.
Co-pending U.S. Appl. No. 14/576,639, Siliu Tan et al., "Hair Styling Compositions Comprising Latex Polymers," filed Dec. 19, 2014 (now U.S. Pat. No. 9,814,668).
Co-pending U.S. Appl. No. 14/577,579, Siliu Tan et al., "Hair Styling Compositions Comprising Latex Polymers and Wax Dispersions," filed Dec. 19, 2014 (now U.S. Pat. No. 9,801,808).
Co-pending U.S. Appl. No. 14/577,740, Christine Shin et al., "Hair Styling Composition Comprising Latex Polymers and a Silicone-Organic Polymer Compound," filed Dec. 19, 2014 (now U.S. Pat. No. 9,814,669).
Co-pending U.S. Appl. No. 14/577,809, Mark Benn, "Hair Coloring Compositions Comprising Latex Polymers," filed Dec. 19, 2014 (now U.S. Pat. No. 9,750,678).

(56) References Cited

OTHER PUBLICATIONS

Co-pending U.S. Appl. No. 14/578,074, Siliu Tan et al., "Compositions and Methods for Hair," filed Dec. 19, 2014.
Co-pending U.S. Appl. No. 14/578,122, Christine Shin, "Hair Cosmetic Composition Containing a Polyurethane Latex Polymer and a Silicone Organic Polymer Compound," filed Dec. 19, 2014.
Co-pending U.S. Appl. No. 14/586,105, Siliu Tan et al., "Compositions and Methods for Hair," filed Dec. 30, 2014.
International Search Report for Application No. PCT/US2014/044036, dated Oct. 21, 2014, 3 pages.
International Search report for Application No. PCT/US2014/044377, dated Oct. 31, 2014, 3 pages.
International Search Report for Application No. PCT/US2014/044557, dated Oct. 13, 2014, 3 pages.
International Search Report for Application No. PCT/US2014/044587, dated Oct. 31, 2014, 3 pages.
International Search Report for Application No. PCT/US2014/044610, dated Oct. 31, 2014, 4 pages.
McKay, Tonya, "Polyquats as Conditioning Agents," naturallycurly.com/curlreading/curl-products/curlchemist-polyquats-as-conditioning-agents, Apr. 5, 2009, [http://www.NATURALLYCURLY.COM/CURLREADING/AUTHORS/TONYAMCKAY/)].
English language abstract for DE 102009054516A1 (Jun. 16, 2011).
English language abstract for DE 2364398A1 (Oct. 30, 1975).
English language abstract for EP 0770375A1 (May 2, 1997).
English language abstract for EP 0847752A1 (Jun. 17, 1998).
English language abstract for EP 0898960A1 (Mar. 3, 1999).
English language abstract for EP 1082953A1 (Mar. 14, 2001).
English language abstract for FR 2633940B3 (Jul. 12, 1991).
English language abstract for FR 2834458A1 (Jul. 11, 2003).
English language abstract for FR 2898050A1 (Sep. 7, 2007).
English language abstract for FR 2961103A1 (Dec. 16, 2011).
English language abstract for FR 2968978A1 (Jun. 22, 2012).
English language abstract for JPH-02-019576 (Jan. 23, 1990).
English language abstract for JPH-05-163124A (Jun. 29, 1993).
English language abstract for KR 20100105168A (Sep. 29, 2010).
Extended European Search Report for counterpart EP Application No. 14817057.4, dated Nov. 2, 2016.
Extended European Search Report for counterpart EP Application No. 14818467.4, dated Nov. 9, 2016.
Extended European Search Report for counterpart EP Application No. 14818460.9, dated Nov. 21, 2016.
Communication Pursuant to Article 94(3) EPC for counterpart EP Application No. 148184674-1114, dated Oct. 1, 2018.
Data Sheet, ACUDYNETM™ 180, "Hair Fixative and Styling Polymer a New Firm Hold, Extremely Low Tack, Fast Drying Polymer for low VOC Hair Care," Dow Personal Care, Sep. 2008.
Data Sheet, ACULYN™ 88, "Rheology Modifier," Dow Personal Care, Apr. 2005.
"Herstellung von Polymer-Filmen gemäß den Angaben im SP (SP, Seite 14, [0117] + [0118])," Image Material.
Lubrizol, "Economy Styling Gel," Oct. 31, 2007.
Lubrizol, "Fixate™ G-100 Hair Fixative Polymer," Technical Data Sheet, Jan. 9, 2003.
Lubrizol, "High Viscosity Hair Gel," Oct. 31, 2007.
Lubrizol "Long-Lasting Hold Spray Gel," Apr. 20, 2015.
Lubrizol, "Spray Hair Gel," Apr. 20, 2015.
Opposition of Beiersdorf to EP Application No. 14817786.8-114, dated Jan. 9, 2019.
Translation of Opposition of Beiersdorf to EP Application No. 14817786.8-114, dated Jan. 9, 2019.
Third European Patent Office for counterpart Application No. 14817057.4-1114, dated Dec. 21, 2018.
Rejection Decision for counterpart CN Application No. 201480048018.7, dated Mar. 29, 2019 (English Translation).
Rejection Decision for counterpart CN Application No. 201480047973.9, dated Mar. 29, 2019 (English Translation).
Non-Final Office Action for copending U.S. Appl. No. 15/852,116, dated Nov. 2, 2018.
Non-Final Office Action for copending U.S. Appl. No. 15/700,586, dated Nov. 6, 2018.
Non-Final Office Action for copending U.S. Appl. No. 15/805,958, dated Nov. 6, 2018.
Final Office Action for copending U.S. Appl. No. 13/931,248, dated Nov. 30, 2018.
Non-Final Office Action for copending U.S. Appl. No. 14/578,122, dated Dec. 18, 2018.
Final Office Action for co-pending U.S. Appl. No. 15/805,958, dated Feb. 14, 2020.
Communication Pursuant to Article 94(3) EPC for counterpart Application No. 15870938.6-1114, dated Jun. 19, 2019.
Communication Pursuant to Article 94(3) EPC for counterpart Application No. 15870940.2-1114, dated Jun. 21, 2019.
Translation of Russian Office Action for counterpart Application No. 2017117254-04, dated Nov. 25, 2019.
Final Office Action for co-pending U.S. Appl. No. 14/578,122, dated Jul. 29, 2019.
Final Office Action for co-pending U.S. Appl. No. 15/700,586, dated May 13, 2019 (vacated Jun. 28, 2019).
Final Office Action for co-pending U.S. Appl. No. 151852,116, dated May 14, 2019 (vacated Jul. 1, 2019).
Final Office Action for co-pending U.S. Appl. No. 15/805,958, dated May 14, 2019 (vacated Jul. 1, 2019).
Non-Final Office Action for co-pending U.S. Appl. No. 15/700,586, dated Jun. 28, 2019.
Non-Final Office Action for co-pending U.S. Appl. No. 15/852,116, dated Jul. 1, 2019.
Non-Final Office Action for co-pending U.S. Appl. No. 15/805,958, dated Jul. 1, 2019.
Preliminary Examination of counterpart Brazilian Patent Application No. BR 112015032458-4, dated Jul. 25, 2019, with Translation.
Preliminary Examination of counterpart Brazilian Patent Application No. BR 112015032471-1, dated Jul. 26, 2019, with Translation.
Brazilian Office Action for counterpart Brazilian Application No. BR112017013122-6, dated Aug. 28, 2019, with Translation.
Brazilian Office Action for counterpart Brazilian Application No. BR112017013117-0, dated Aug. 27, 2019, with Translation.
Translated Chinese Reexamination Notification for counterpart Application No. 201480048018.7, dated Jul. 3, 2020.
Notice of Allowance for copending U.S. Appl. No. 15/852,116, dated Mar. 5, 2020.
Final Office Action for copending U.S. Appl. No. 15/700,586, dated Mar. 31, 2020.
Russian Office Action for counterpart Application No. 2017117249-49, dated Mar. 17, 2020.
Sutyagin, V.M. et al., Chemistry and Physics of Polymers: Study Book—Tomsk: Publ. Office of TPU, 2003, p. 142—translated.
European Notice of Allowance for counterpart Application No. 14817057-4, dated May 4, 2020.
Translated Brazilian Office Action for counterpart Application No. BR112015032471-1, dated Apr. 8, 2020.
Translated Brazilian Office Action for counterpart Application No. BR112015032458-4, dated Apr. 8, 2020.
Mintel: "Hi-Lights Cognac Hair Mascara," Frederic Fekkai, XP-002780869, Oct. 2007.
Mintel: "24 Saat 24 Hour Hair Care Cream for Straight Hair," Canan Kozmetik, XP-002780868, Dec. 2004.
Mintel: "Moisturizing Modeler," Acquaffora Forma, XP-002780867, Sep. 2013.
Russian Office Action for counterpart Application No. 2017117249-04, dated Sep. 13, 2019.
Russian Office Action for counterpart Application No. 2017117254-04, dated Sep. 13, 2019.
European Office Action for counterpart EP Application 148184674-1114, dated Mar. 12, 2018.
Japanese Office Action for counterpart JP Application 2016-523878, dated Apr. 27, 2018 with translation.
Japanese Office Action for counterpart JP Application 2016-524247, dated Apr. 27, 2018 with translation.
Final Office Action for copending U.S. Appl. No. 14/578,122, dated May 29, 2018.

(56) References Cited

OTHER PUBLICATIONS

Mexican Office Action for counterpart MX Application No. MX/a/2015/017044, dated Apr. 29, 2018 (translation of requirements stated by Examiner only).
European Office Action for counterpart EP Application No. 148170574-1114, dated Apr. 20, 2018.
European Office Action for counterpart EP Application No. 148184609-1114, dated Mar. 29, 2018.

* cited by examiner

COMPOSITIONS AND METHODS FOR TREATING HAIR

This is a continuation of application Ser. No. 13/931,222, filed Jun. 28, 2013, which is incorporated herein by reference.

TECHNICAL FIELD

The disclosure relates to hair styling compositions comprising at least two latex polymers, wherein at least one latex polymer is a film-forming polymer. The at least two latex polymers are chosen from acrylate polymers. In various embodiments of the disclosure, the at least two latex polymers are chosen to have certain properties. Compositions comprising the at least two latex polymers may, according to certain embodiments, form films that have surprising properties. Methods of styling the hair with such compositions are also disclosed.

BACKGROUND

Compositions for styling the hair are known, such as, for example, hair spray compositions, hair gels and mousses, hair volumizing compositions, hair smoothing creams, lotions, serums, oils, clays, etc. The goals of many hair styling compositions include to hold or fix the hair in a particular shape, to impart or increase volume of the hair, and/or to smooth the hair, e.g. to decrease or eliminate the appearance of frizz.

Drawbacks associated with current products for styling the hair include that the product is often sticky or tacky and/or often produces a film that imparts a sticky or tacky feel, and styled hair that is stiff and/or "crunchy" (i.e. the film is hard and brittle resulting in a crunching feel or sound when the hair is touched), which is undesirable for most consumers.

Current products for styling the hair typically include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film. These products also tend to exhibit problems with product spreadability, hair manageability, and low degree of humidity resistance which is particularly a problem in hot and humid countries.

The use of latex polymers is also known, for example, to provide extended-wear properties to a cosmetic product (e.g. mascara, eyeliner, nail polish) into which they are formulated.

Some known compositions include one latex polymer. For example, U.S. Pat. No. 6,126,929 describes a composition comprising a dispersion of a latex film former, optionally with a plasticizer, and a non film-forming particle not capable of being film-formed. U.S. Pat. No. 4,710,374 describes a composition comprising cationic polymers, a surfactant, and an anionic latex. U.S. Pat. No. 7,740,832 describes a composition comprising at least one non-latex polymer and an anionic, cationic or amphoteric fixing polymer. U.S. Pat. No. 4,798,721 describes a composition comprising a latex particle. U.S. Patent Application No. 2005/0089490 A1 describes a composition comprising a water-dispersible styling polymer and a gel-forming polymer.

Other known cosmetic compositions include various components to provide improved properties such as adhesion, flexibility, and compatibility of other components. For example, U.S. Patent Application No. 2007/0224140 A1 describes a composition comprising a cosmetically acceptable medium, a non film-forming microsphere to provide adhesion, and a film-forming component comprising two water-borne emulsion polymers. French Patent Application No. FR 2 968 978A describes an eyeliner composition comprising at least two film-forming latexes and a plasticizer to increase the flexibility of the film. French Patent Application No. FR 2 898 050A describes a composition comprising a fatty acid ester, and a copolymer of a (meth) acrylate polymer and a hydroxyester (meth)acrylate. U.S. Patent Application No. 2009/0297467A describes a composition comprising at least one neutralized sulfonated polymer and mixtures of acrylates and hydroxyester acrylates. U.S. Patent Application No. 2009/035335 A1 describes a mascara composition comprising two water-dispersible acrylate polymers, and a cross-linked polymeric film-former to enhance the compatibility and bind the two water-dispersible acrylate polymers. International Patent Application No. WO 2011/137338 A2 describes a composition comprising a acrylate dispersion and an acrylic film-forming dispersion. U.S. Patent Application No. 2004/0071646A describes an aerosol device containing a composition comprising a polyurethane dispersion having a particle size of from 0.1-1 μm, and at least one non-latex fixing polymer.

Additionally, some cosmetic compositions incorporate polymers having a core-shell structure. For example, U.S. Patent Application No. 2003/0064045 A1 describes a mascara composition comprising a dispersion of particles having a core-shell structure. U.S. Patent Application No. 2007/0286833 A1 describes a multistage polymer comprising a latex core-shell particle comprising a soft polymer and a hard polymer. In addition, U.S. Patent Application No. 2009/0317432A describes an applicator for makeup containing a composition comprising a colorant and at least one latex or core-shell latex particle.

Cosmetic compositions in a non-aqueous medium are known. For example, European Patent Application No. EP 1 082 953A describes a dispersion comprising two film formers in isododecane. International Patent Application No. WO11056332A describes a composition comprising three volatile solvents, and at least one film former, for example silicon acrylate or acrylate, soluble or dispersible in at least one of the three solvents.

Compositions for use in mascaras may have low glass transition temperatures ("Tg") to obtain a soft film. For example, U.S. Patent Application No. 2010/0028284 A1 describes a mascara composition comprising at least two acrylate film formers, where the glass transition temperature ("Tg") of the mascara composition is ≤20° C. U.S. Patent Application No. 2006/134043A describes a mascara composition comprising a fatty acid and at least one acrylate resin emulsion.

Some known compositions use solubilized polymers rather than polymer particles. For example, U.S. Pat. No. 7,651,693 describes a composition comprising a solubilized blend of two polymers. U.S. Pat. No. 6,214,328 describes a composition comprising at least one acrylate latex that is soluble in solutions containing low volatile organic compounds or in water upon neutralization.

U.S. Pat. No. 5,441,728 describes a composition comprising a water-soluble fixative polymer and a latex particle.

Water-soluble polymers tend to be sticky, and may not be suitable for applications requiring a clean touch.

French Patent Application No. FR 2 834 458A describes a nail polish composition comprising two film formers in an aqueous medium in a specific ratio.

However, it has now been discovered that by providing a composition comprising at least two latex polymers chosen from acrylate polymers, wherein at least one of said latex polymers is a film-forming polymer, it is possible to form a film on a substrate that has certain desirable properties, such as a clean, natural, and/or "invisible" feel, and a lack of stickiness. Such compositions may be useful in hair-styling applications wherein styling benefits such as natural look, curling or straightening, and styling hold are imparted to hair.

Moreover, compositions according to embodiments of the disclosure may be prepared that deliver a surprisingly broad range of hair styling benefits, such as, for example, from low to high style-hold and curl-retention properties, for example by varying the weight ratio between both latex acrylate polymers, with or without additives.

DESCRIPTION OF EXEMPLARY EMBODIMENTS

The disclosure relates, in various embodiments, to compositions comprising at least two latex acrylate polymers, wherein at least one latex acrylate polymer is a film-forming polymer. In various embodiments, the at least two latex acrylate polymers may be chosen to have certain properties. In at least certain embodiments, the at least two latex acrylate polymers are present in a combined amount ranging from about 0.1% to about 30% by weight, relative to the weight of the composition. In further embodiments, the at least two latex acrylate polymers are present in the composition in a weight ratio of about 10:1 to about 1:10.

The composition comprising the at least two latex acrylate polymers forms a film when applied to a substrate. The film may, according to at least certain embodiments of the disclosure, have a Young's modulus ranging from about 0.05 MPa to about 5 GPa, and/or a strain under stress at 0.5 MPa that ranges up to about 300%. By way of example only, the film may have a Young's modulus ranging from about 80 MPa to about 5 GPa and a strain, under stress at 0.5 MPa, ranging from about 0.01% to less than about 1%. By way of further example, the film may have a Young's modulus ranging from about 5 MPa to about 100 MPa and a strain, under stress at 0.5 MPa, ranging from about 0.5% to less than about 20%. By way of yet further example, the film may have a Young's modulus ranging from about 0.05 MPa to about 5 MPa and a strain, under stress at 0.5 MPa, ranging from about 10% to about 300%.

In at least certain exemplary embodiments according to the disclosure, the resulting film formed by the composition comprising at least two latex acrylate polymers, wherein at least one latex polymer is a film-forming polymer, is clear and/or transparent.

In further embodiments, methods of styling the hair are disclosed, said methods comprising applying compositions according to the disclosure to the hair. Such styling methods may comprise shaping, reshaping, positioning, repositioning, adding volume to, curling, or straightening the hair, in order to achieve a certain hair style or appearance.

Latex Polymers

According to various exemplary embodiments of the disclosure, the at least two latex polymers, at least one of which is a film-forming polymer, are chosen from acrylate polymers. The at least two latex acrylate polymers may be present in a combined amount ranging from about 0.1% to about 30% by weight, relative to the weight of the composition. In other embodiments, the at least two latex acrylate polymers may be present in the composition in a weight ratio of about 10:1 to about 1:10.

In various embodiments, the at least two latex acrylate polymers, at least one of which is a film-forming polymer, may be identified as polymer A and polymer B. Compositions according to certain embodiments may comprise at least one polymer A and at least one polymer B, wherein at least one of polymer A and polymer B is a film-forming polymer.

In various embodiments, polymer A may be chosen from latex acrylate polymers having a Young's modulus ranging from about 0.1 MPa to about 10 MPa, and a strain, under stress at 0.5 MPa, of at least about 1%; and polymer B may be chosen from latex acrylate polymers having a Young's modulus ranging from about 10 MPa to about 6 GPa, and a strain, under stress at 0.5 MPa, of less than about 5%. In at least certain embodiments, polymer A may have a glass transition temperature (Tg) ranging from about −90° C. to about 40° C., and polymer B may have a glass transition temperature (Tg) ranging from about 40° C. to about 200° C.

In at least certain other embodiments, the weight ratio of polymer A to polymer B in the compositions of the disclosure is from about 1:10 to about 1:1, from about 3:1 to about 10:1, or from about 5:1 to about 10:1.

In at least certain exemplary and non-limiting embodiments, latex acrylate polymers A and B may be chosen such that polymer A comprises at least one latex acrylate polymer which is optionally a film-forming polymer that is a relatively soft, flexible latex polymer, and polymer B comprises at least one latex acrylate polymer which is optionally a film-forming polymer that is a relatively hard, brittle polymer, although such characteristics are not required.

At least one of polymer A and polymer B is a film-forming polymer. In various exemplary embodiments, latex polymer A is a film-forming polymer and latex polymer B is a non-film-forming polymer. In further exemplary embodiments, latex polymer A is a non-film-forming polymer and latex polymer B is a film-forming polymer. In yet further exemplary embodiments, latex polymer A is a film-forming polymer and latex polymer B is a film-forming polymer.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By "at least two latex acrylate polymers," it is contemplated that more than two latex acrylate polymers may be chosen. Thus, for example, in various embodiments, both polymers A and B in the compositions of the disclosure may be latex film-forming acrylate polymers, and the composition may also comprise at least one latex polymer that is a non-film-forming acrylate polymer; or one of polymer A and B may be a film-forming acrylate polymer while the other is a non-film-forming acrylate polymer, but at least one additional film-forming (latex or non-latex) polymer may also be added; and so on.

In further embodiments, the composition comprises exactly two latex acrylate polymers, at least one of which is a film-forming polymer. In yet further embodiments, the composition comprises at least two latex acrylate polymers, one or both of which are film-forming polymers, but does not comprise any additional film-forming polymers.

In at least certain embodiments of the disclosure, the at least two latex polymers are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 µm. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex acrylate polymers may, in various exemplary embodiments, exist as dispersed polymer particles in a dispersion medium, such as an aqueous dispersion medium. The latex acrylate polymers may, in certain embodiments, each be dispersed in independent dispersion media. In yet further embodiments, the latex acrylate polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex acrylate polymers may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex acrylate polymers is retained in the dispersion medium.

In further embodiments, the latex acrylate polymers may be chosen from uncharged and charged latex polymers. Thus, the latex acrylate polymers may, according to various exemplary embodiments, be chosen from nonionic latex acrylate polymers, cationic latex acrylate polymers, and anionic latex acrylate polymers.

As non-limiting examples of latex acrylate polymers that may be used, mention may be made, independently, of acrylate latex polymers such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth) acrylic, cyclohexyl (meth)acrylic, isohexyl (meth)acrylic, heptyl (meth)acrylic, isoheptyl (meth)acrylic, octyl (meth) acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth) acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth) acrylate, isopropyl oxide (meth)acrylate, butyl oxide (meth) acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth)

acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth)acrylate, N,N-diethyleaminoethyl (meth)acrylate, and N,N,N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl (meth) acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment.

In at least certain, non-limiting exemplary embodiments, acrylic latex polymers may be chosen from aqueous dispersions of Methacrylic Acid/Ethyl Acrylate copolymer (INCI: Acrylates Copolymer, such as Luviflex® Soft by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as Fixate Superhold™ by Lubrizol), Styrene/Acrylic copolymer (such as Neocryl® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as Daitosol 5000AD, Daito Kasei Kogyo), and Acrylic copolymers and Acrylates Copolymers, such as those known under the tradenames VINYSOL 2140 (Daido Chemical), ACULYN™ 33 (Dow Chemical), LUVIMER® MAE (BASF), or BALANCE CR (AKZO NOBEL).

In various embodiments according to the disclosure, it may be possible to choose a polymer that comprises both acrylate and polyurethane parts at the molecular level.

Compositions

As described herein, exemplary compositions according to the disclosure may comprise at least two latex polymers chosen from acrylate polymers, wherein at least one of the latex acrylate polymers is a film-forming polymer. In certain embodiments, each of the latex acrylate polymers is present in an amount ranging from about 0.05% to about 10% by weight, such as about 0.1% to about 7.5% by weight, such as about 0.25% to about 5% by weight, such as about 0.5% to about 2.5% by weight, or about 0.5% to about 1.5% by weight, relative to the weight of the composition, including all ranges and subranges there between. In other embodiments, each of the latex acrylate polymers is present in an amount ranging from about 1% to about 15% by weight, such as about 1% to about 12% by weight, such as about 1.2% to about 12% by weight, such as about 1.5% to about 10% by weight, or such as less than about 10% by weight, relative to the weight of the composition, including all ranges and subranges there between. In yet other embodiments, each of the latex acrylate polymers is present in an amount ranging from about 0.1% to about 2% by weight, such as about 0.15% to about 1.9% by weight, or such as about 0.18% to about 1.8% by weight, relative to the weight of the composition, including all ranges and subranges there between.

In certain embodiments, the latex acrylate polymers are present in a combined amount ranging from about 0.1% to about 30% by weight, such as about 0.1% to about 25% by weight, such as about 0.2% to about 20% by weight, such as about 0.2% to about 15% by weight, such as about 0.5% to about 10% by weight, such as about 1% to about 8% by weight, such as about 1% to about 5% by weight, such as about 1% to about 3% by weight, or such as below about 30% by weight, or such as about 25% by weight, or such as about 20% by weight, relative to the weight of the composition, including all ranges and subranges there between. By way of non-limiting example, the combined amount of latex acrylate polymers may be about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight, relative to the weight of the composition.

In yet further embodiments, the combined amount of latex acrylate polymers ranges up to about 30%, such as up to about 29%, such as up to about 28%, such as up to about 27%, such as up to about 26%, such as up to about 25%, such as up to about 24%, such as up to about 23%, such as up to about 22%, such as up to about 21%, such as up to about 20%, such as up to about 19%, up to about 18%, up to about 17%, up to about 16%, up to about 15%, up to about 14%, up to about 13%, up to about 12%, up to about 11%, up to about 10%, up to about 10%, up to about 9%, up to about 8%, up to about 7%, up to about 6%, up to about 5%, up to about 4%, up to about 3%, up to about 2%, or up to about 1%, each by weight, relative to the weight of the composition. In at least one exemplary embodiment, the combined amount of latex acrylate polymers is less than about 10% by weight, such as less than about 5% by weight, relative to the weight of the composition.

According to various embodiments of the disclosure, the weight ratio of the at least two latex acrylate polymers, e.g.

polymer A to polymer B, may range from about 10:1 to about 1:10, such as about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2, including all ranges and subranges there between. It should be understood that when polymer A and/or polymer B comprise at least one latex film-forming polymer, the weight ratio includes the total amount of polymer A and/or polymer B.

According to various embodiments of the disclosure, the weight ratio of polymer A to polymer B is about 10:1, about 9:1, about 8:1, about 7:1, about 6:1, about 5:1, 4:1, about 3:1, about 2:1, about 1:1, about 1:2, about 1:3, about 1:4, about 1:5, about 1:6, about 1:7, about 1:8, about 1:9, or about 1:10.

In at least certain exemplary and non-limiting embodiments, when polymer A is chosen from latex acrylate polymers having a Young's modulus ranging from about 0.1 MPa to about 10 MPa, and a strain, under stress at 0.5 MPa, of at least about 1%; and polymer B is chosen from latex acrylate polymers having a Young's modulus ranging from about 10 MPa to about 6 GPa, and a strain, under stress at 0.5 MPa, of less than about 5%, different weight ratios of polymer A to polymer B may be chosen to correspond to different hair styling applications. By way of example only, a weight ratio of polymer A to polymer B ranging from about 1:10 to about 1:1 may, in some embodiments, provide a high level of style hold; a weight ratio of polymer A to polymer B ranging from about 5:1 to about 10:1 may, in some embodiments, provide a medium to high level of style hold; and a weight ratio of polymer A to polymer B ranging from about 3:1 to about 10:1 may, in some embodiments, provide a light to medium level of style hold.

In addition to the at least two latex acrylate polymers, wherein at least one is a film-forming polymer, the compositions may further comprise at least one solvent. The at least one solvent may be chosen from water, at least one cosmetically acceptable organic solvent, or a mixture of water and at least one cosmetically acceptable organic solvent. Cosmetically acceptable organic solvents may, in various embodiments, be water-miscible, e.g. a mixture capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

The at least one solvent may be present in an amount ranging up to about 95%, such as from about 1% to about 90%, from about 5% to about 80%, or from about 10% to about 60% by weight, relative to the total weight of the composition.

In at least certain exemplary embodiments, the latex polymer particles are not soluble in the solvent of the composition, and thus remain in particulate form even after evaporation of the solvent. For example, in embodiments where the composition comprises alcohol as a cosmetically acceptable organic solvent, the latex particles may remain in particulate form upon evaporation of the alcohol, such as once the composition is applied to a substrate.

Compositions according to various embodiments of the disclosure may further comprise additional components that are typically used in hair styling compositions. Such components are known to those of skill in the art, or are within the ability of those of skill in the art to determine depending on the particular application, such as, for example, the particular component and/or amount thereof. Such components include, but are not limited to, coalescents, plasticizers, and thickening agents.

In various embodiments, the composition described herein may have a pH ranging from about 2 to about 9, such as about 3 to about 8, or about 4 to about 7.

In at least certain exemplary embodiments, the compositions are in the form of hair styling compositions, in any form, such as, for example, a gel, a cream, a foam, a lotion, an emulsion, or a liquid that may be sprayed onto or otherwise applied to the hair. In various embodiments, the composition may be provided in the form of a gel, a mousse, or a spray. In at least certain embodiments, the composition may be applied to the hair by first applying to the hands, and then contacting the hair with the hands; in other embodiments, the composition may be applied directly onto the hair, such as by spraying. The compositions may, in various embodiments, be applied to the hair as a leave-on treatment.

In various embodiments, the application of an external stimuli, such as heat, may be desirable as part of the hair styling process. By way of example only, before, during, or after the composition is applied to wet or dry hair, the hair may optionally be further treated with an external stimuli, for example with heat ranging from about 25° C. to about 250° C. In at least certain embodiments, the hair may also be shaped or positioned as desired while exposed to external stimuli, such as while heated or exposed to heat.

Professional and consumer heating tools can be used as a means to deliver heat or an elevated temperature to the hair. The heating tools can generate heat through electrical current or heating lamps. Depending upon the desired style, these tools include, but are not limited to, heaters, blow dryers, flat irons, hot combs, hot curler sets, steam pods, heated crimpers, heated lash curlers, heated wands/brushes, and hood driers or their combinations thereof.

As described, compositions according to the disclosure may impart a film on a substrate, such as on the hair or on the hand during or after application to the hair. A film formed by the composition may, surprisingly, be clean-feeling and not sticky, as with traditional hair styling compositions. Also surprisingly, the composition may impart a film on the hair that leaves the hair relatively natural and clean-feeling, yet has a flexible coating, leaving little to no residue, allows the hair to be bouncy and springy with little to no frizz or flaking, may impart relatively high definition with individualized curls, style control, volume, and shine, and/or may allow for relatively long-lasting hold and style memory. Furthermore, in at least certain embodiments according to the disclosure, the compositions are not sticky or tacky. A user of hair compositions according to various embodiments described herein may thus feel that the composition is not perceptible or is "invisible," yet still effectively style and/or hold the hair. Additionally, the compositions may have effective hair styling and/or hold properties, even in conditions of high, or relatively high, humidity. In at least certain embodiments according to the disclosure, the compositions may be quick-drying, which may allow drying and/or styling time to be reduced, as well as further improve ease of styling and curl retention.

Furthermore, as described, compositions prepared according to various embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable. By altering the weight ratio of the first and second polymers, it is possible to formulate compositions having high levels of style hold, medium to high levels of style hold, medium levels of style hold, or light to medium levels of style hold.

In at least certain embodiments, a film formed by the compositions described herein may be clear and/or stable. In such embodiments, phase separation and dramatic aggregation are minimized.

In addition, hair styled or treated with compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure.

It should be noted, however, that compositions and films, as well as hair to which the composition or film has been applied, according to the disclosure may not have one or more of the herein-referenced properties, yet are intended to be within the scope of the disclosure.

Also disclosed herein are methods for styling the hair, said methods comprising applying a composition according to the disclosure to the hair, either before, during, or after styling the hair. One or more steps of treating the hair with an external stimuli, such as heat, before, during, or after the composition has been applied to the hair are also contemplated.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a surfactant" is intended to mean at least one surfactant.

Unless otherwise indicated, all numbers used in the specification and claims are to be understood as being modified in all instances by the term "about," whether or not so stated. The term "about" as it modifies numbers herein is meant to indicate a difference of 10% or less from the stated number, such as 9% or less, such as 8% or less, such as 7% or less, such as 6% or less, such as 5% or less, such as 4% or less, such as 3% or less, such as 2% or less, or such as 1% or less, in various exemplary embodiments. Thus, by way of example only, in one embodiment where "about" indicates a difference of 10% or less, the phrase "about 20%" is intended to encompass a range from 18%-22%. In another exemplary embodiment where "about" indicates a difference of 5% or less, the phrase "about 20%" is intended to encompass a range from 19%-21%. All such numbers within each specified range are hereby explicitly intended to be included in the disclosure.

It should also be understood that the precise numerical values used in the specification and claims form additional embodiments of the disclosure, and are intended to include any ranges which can be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

It should be understood that compositions according to various embodiments of the disclosure form a film when applied to a substrate. However, the various properties of the film described herein are intended to include any film provided by compositions according to the disclosure, regardless of whether the film is attached or bonded to the substrate or not. By way of example only, once the compositions are applied to a substrate and a film is formed, the film may subsequently be removed in order to evaluate properties such as strain and Young's modulus.

EXAMPLES

The following Examples are intended to be non-restrictive and explanatory only, with the scope of the invention being defined by the claims.

Procedures

A. Procedures for Determination of Physical Properties of Films

Film plating: The latex film was obtained by allowing a 30 gram water solution containing 4 grams of the latex polymer(s) to dry slowly in a 100 mL PFA Petri dish (100 mm diameter×15 mm height) at room temperature for at least 3 days.

Film measurement: The latex film, with known dimensions (length, width, thickness), was mounted on the Q800 Dynamic Mechanical Analysis from TA Instrument, and tested in a DMA Control Force mode. The stress/strain test was obtained using the following procedure:

Preload force: 0.001 N
Isothermal: 25° C.
Soak time: 0.5 minutes
Force ramp rate: 0.5 MPa/min to 18 N The test ended when the sample broke, 18 N force was reached, or maximum displacement was achieved (25.5 mm).

From the stress/strain curve, the Young's Modulus was calculated as the slope of the linear portion at about 0.01% Strain to about 1% Strain. From the stress/strain curve, the % Strain at the stress of 0.5 MPa was also reported.

A high Young's Modulus demonstrates a hard film, while a lower Young's Modulus represents a more elastic film. A high Strain demonstrates a stretchy, elastic film, while a lower Strain represents a more brittle film.

B. Procedure for Determination of Mechanical Properties of Hair Treated with Latex Compositions Hair treatment: A strip of regular bleached hair (from IHIP, 1 cm in width, 16 cm long, about 2.0-2.5 g of hair) was treated with the latex solution (0.75 g of solution/g hair). The hair was combed through until the solution was uniformly distributed over the surface of the tress. The treated hair was allowed to dry overnight at room temperature.

Hair measurement: Three-point bending measurements were conducted using a texture analyzer (Model TA-XTPlus, Texture Technologies Corporation) equipped with a hair mounting accessory as described in *J. Cosmet.*

Sci., 53, 345-362 (November/December 2002). The cantilever bending experiment consisted of the following sequence of steps: the hair tress was placed on a 2-point of 6 cm width, and the probe, representing the third point, came down at the middle of the hair tress and performed 10 cycles of 10-mm deformations of the hair tress. The testing protocol was:

Test mode=Compression
Pre-test speed=2 mm/sec
Test speed=2 mm/sec
Post-test speed=2 mm/sec
Target mode=Distance
Distance=10 mm
Count=10
Trigger type=Auto (Force)
Trigger force=1 g After finishing 10 cycles of bending, a plot of force as a function of distance of 10 deformations was generated. From the plot, the maximum force in the first (F1) and the tenth (F10) deformation cycle was determined. The change from F1 to F10 was calculated from:

(F1−F10)/F1×100.

A high maximum force indicated that the hair was stiff and rigid, and a lower maximum force indicated that the hair was softer and more flexible.

Each experiment was run three times, and the results are reported from the average of the three experiments.

C. Procedure for Determination of Curl Retention in High Humidity of Hair Treated with Latex Compositions Hair treatment: Regular bleached hair swatch (from IHIP, 14.5 cm long, about 0.5 g) was treated with a solution of 2% latex polymers (0.5 g solution/g hair). The hair was combed until the solution was uniformly distributed over the hair swatch surface. The treated hair was then rolled onto a spiral rod (0.5 in diameter) and allowed to dry at room temperature overnight.

Curl retention measurement: The coiled hair was removed from the rod and placed in the humidity chamber at 95% RH, 25° C. for 24 hours. The Curl Retention was calculated as:

(Lo−Lf)/(Lo−Li)×100 wherein Lo=fully extended hair length, Li=initial coiled hair length before humidity exposure, and Lf=final hair length after 24 hours exposure.

Compositions containing latex polymers were evaluated according to the methods described above. The weight of each latex polymer in the following examples is determined on a dry weight basis.

Example 1: Evaluation of Acrylate Latexes

Clear films were obtained from the combination of DAITOSOL 5000AD (INCI name: Acrylates Copolymer, Young's Modulus of 0.4 MPa and strain, under stress at 0.5 MPa, of >150%; polymer A) and FIXATE SUPERHOLD™ (INCI name: Polyacrylate-2 Crosspolymer, Young's Modulus of 1151 MPa and strain, under stress at 0.5 MPa, of 0.01%; polymer B) at various latex polymer ratios. Their physical properties are shown in Table 1A below.

TABLE 1A

| Sample | Component (A:B) | Young's Modulus (MPa) | Strain at 0.5 MPa stress (%) |
|---|---|---|---|
| 1a | Polymer A only | 0.4 | >150 |
| 1b | 1:10 | 1104 | 0.01 |
| 1c | 1:5 | 835 | 0.03 |
| 1d | 1:3 | 730 | 0.06 |

TABLE 1A-continued

| Sample | Component (A:B) | Young's Modulus (MPa) | Strain at 0.5 MPa stress (%) |
|---|---|---|---|
| 1e | 1:1 | 519 | 0.09 |
| 1f | 3:1 | 164 | 0.41 |
| 1g | 5:1 | 33 | 3.94 |
| 1h | 10:1 | 3 | 145.30 |
| 1i | Polymer B only | 1151 | 0.01 |

Clear films were obtained from the association of VINYSOL 2140 (Acrylic Copolymer, Young's Modulus of 2 MPa and strain, under stress at 0.5 MPa, of >200%; polymer A) and ACULYN 33™ (INCI name: Acrylates Copolymer, Young's Modulus of 2096 MPa and strain, under stress at 0.5 MPa, of 0.01%; polymer B) at various latex polymer ratios. Their physical properties are shown in Table 1B below.

TABLE 1B

| Sample | Component (A:B) | Young's Modulus (MPa) | Strain at 0.5 MPa stress (%) |
|---|---|---|---|
| 1j | Polymer A only | 2 | >200 |
| 1k | 1:10 | 1868 | 0.02 |
| 1l | 1:5 | 1200 | 0.02 |
| 1m | 1:3 | 1062 | 0.04 |
| 1n | 1:1 | 228 | 0.30 |
| 1o | 3:1 | 24 | 12.07 |
| 1p | 5:1 | 8 | 89.27 |
| 1q | 10:1 | 3 | >100 |
| 1r | Polymer B only | 2096 | 0.01 |

The results in Tables 1A and 1B show that by varying the ratio of the two latex polymers, it is possible to control the hardness (not as hard as Polymer A and not as soft as Polymer B) and flexibility (not as brittle as Polymer A and not as stretchy as Polymer B) of films produced according to various embodiments of the disclosure.

Example 2: Evaluation of Hair Treated with Acrylate Latexes

Hair tresses were treated with 2% solutions of DAITOSOL 5000AD (polymer A) and FIXATE SUPERHOLD™ (polymer B) and at various latex polymer ratios. Their mechanical properties are shown in Table 2A below.

TABLE 2A

| Sample | Component (A:B) | F1 (g) | Change in F (%) |
|---|---|---|---|
| 2a | Polymer A only | 124 | 36 |
| 2b | 1:10 | 1905 | 44 |
| 2c | 1:5 | 2008 | 40 |
| 2d | 1:3 | 1749 | 35 |
| 2e | 1:1 | 1443 | 27 |
| 2f | 3:1 | 653 | 29 |
| 2g | 5:1 | 515 | 32 |
| 2h | 10:1 | 375 | 34 |
| 2i | Polymer B only | 2091 | 44 |

Hair tresses were treated with 2% solutions of VINYSOL 2140 (polymer A) and ACULYN 33™ (polymer B) at various latex polymer ratios. Their mechanical properties are shown in Table 2B below.

TABLE 2B

| Sample | Component (A:B) | F1 (g) | Change in F (%) |
|---|---|---|---|
| 2j | Polymer A only | 249 | 41 |
| 2k | 1:10 | 1081 | 65 |
| 2l | 1:5 | 1334 | 60 |
| 2m | 1:3 | 1386 | 61 |
| 2n | 1:1 | 1189 | 35 |
| 2o | 3:1 | 761 | 53 |
| 2p | 5:1 | 636 | 45 |
| 2q | 10:1 | 475 | 52 |
| 2r | Polymer B only | 1339 | 67 |
| 2s | Commercial 1* | 1835 | 76 |

*Main ingredients: VP/VA copolymer, polyquaternium-11, PEG 90 M, PEG-40 hydrogenated castor oil, acrylates/C10-30 alkyl acrylate crosspolymer, alcohol denatured.

These results show that hair tresses treated with various ratios of the two latex polymers display a wide variety of rigidity, flexibility, stiffness, and softness. Compared to a commercial product (no latex), they show a significantly better styling durability due to the lower change in the maximum force after 10 cycles of deformation.

Example 3: Evaluation of High Humidity Curl Retention of Hair Treated with Acrylate Latexes Hair swatches were treated with 2% solutions of DAITOSOL 5000AD (polymer A) and FIXATE SUPERHOLD™ (polymer B) at various latex polymer ratios. The high humidity curl retention results are shown in Table 3A below.

TABLE 3A

| Sample | Component (A:B) | Curl Retention (%) |
|---|---|---|
| 3a | Polymer A only | 29 |
| 3b | 1:10 | 82 |
| 3c | 1:5 | 80 |
| 3d | 1:3 | 82 |
| 3e | 1:1 | 80 |
| 3f | 3:1 | 59 |
| 3g | 5:1 | 44 |
| 3h | 10:1 | 38 |
| 3i | Polymer B only | 71 |

Hair swatches were treated with 2% solutions of VINYSOL 2140 (polymer A) and ACULYN 33™ (polymer B) at various latex polymer ratios. The high humidity curl retention results are shown in Table 3B below.

TABLE 3B

| Sample | Component (A:B) | Curl Retention (%) |
|---|---|---|
| 3j | Polymer A only | 39 |
| 3k | 1:10 | 87 |
| 3l | 1:5 | 73 |
| 3m | 1:3 | 83 |
| 3n | 1:1 | 76 |
| 3o | 3:1 | 59 |
| 3p | 5:1 | 49 |
| 3q | 10:1 | 49 |
| 3r | Polymer B only | 82 |

These results show that addition of the second latex improves the curl retention, compared to the individual latexes.

Example 4: Evaluation of Effects of Concentration on Performance on Treated Hair Regular bleached hair was treated with solutions of 1:1 ratio of FIXATE SUPERHOLD and DAITOSOL 5000AD at various latex polymer concentrations. The three-point bending test and the high humidity curl retention test was performed as described above. The results are shown in Table 4 below.

TABLE 4

| Sample | Concentration | F1 (g) | Curl Retention (%) |
|---|---|---|---|
| 4a | 1% | 675 | 81 |
| 4b | 2% | 1207 | 86 |
| 4c | 5% | 2183 | 88 |
| 4d | None (commercial 1*) | 1835 | 42 |
| 4e | None (commercial 2**) | 4394 | 58 |

*Main ingredients: VP/VA copolymer, polyquaternium-11, PEG 90 M, PEG-40 hydrogenated castor oil, acrylates/C10-30 alkyl acrylate crosspolymer, alcohol denatured.
**Main ingredients: Water, Acrylates/steareth-20 methacrylate crosspolymer, polyquaternium-69, PVP, sorbitol and alcohol denatured.

The results demonstrate that as the concentration of the latexes increases, the hardness of the styled hair increases, as well as an increase in curl retention. It is noted that while having a wide range of hold, styled hair shows a significantly better hydrophobicity and humidity resistance compared to that treated with commercial (no latex) products.

Example 5: Evaluation of Neutralized Latex Polymer vs. Unneutralized Latex Polymer Combinations of aqueous dispersions comprising latex polymers neutralized to 100% with an amine (Aminomethyl propanol, AMP) were compared with aqueous dispersions comprising unneutralized latex acrylate polymers.

TABLE 5A

| | Test Composition A | Control Composition A | Test Composition B | Control Composition B |
|---|---|---|---|---|
| LUVIFLEX® SOFT Acrylates copolymer, Young's Modulus of 2758 MPa and strain, under stress at 0.5 MPa, of <0.01% | 1 g | 1 g | — | — |
| LUVIFLEX® MAE Acrylates copolymer, Young's Modulus of 385 MPa and strain, under stress at 0.5 MPa, of <1% | 1 g | 1 g | 1 g | 1 g |

TABLE 5A-continued

| | Test Composition A | Control Composition A | Test Composition B | Control Composition B |
|---|---|---|---|---|
| ACUDYNE ™ DHR Acrylates/hydroxyesters Acrylates Copolymer, Young's Modulus of 56 MPa and strain, under stress at 0.5 MPa, of 2.68% | — | — | 1 g | 1 g |
| AMP | — | 0.65 g | — | 0.67 g |
| Deionized water | QS to 100 g | QS to 100 g | QS to 100 g | QS to 100 g |
| pH | 3.61 | 6.37 | 3.66 | 8.25 |
| Appearance | milky | crystal clear | milky | crystal clear |

Male mannequin hair was dampened with water. Next, 1 gram of Test Composition A was applied onto one side of the hair, and evenly distributed as a hair spiking product with bare hands. One gram of the Control Composition A, which was neutralized, was applied to the other side. The product was allowed to dry on the hair at ambient conditions.

The same procedure was followed with Test Composition B and Control Composition B.

It was observed that, during application of Control Compositions A and B, the products foamed/creamed on hair, had more viscosity, and felt very sticky and heavy on hair and hands. However, Test Compositions A and B were applied onto the hair very cleanly, invisibly, and without any tack or stickiness on hair or the hands.

Further, curl retention at 90% relative humidity was performed and showed that, after 24 hours, both control (with AMP) swatches elongated more (held the curl less) than the respective test (without AMP) swatches. The results are set forth in Table 5B.

TABLE 5B

| Sample | Final length (cm) | Initial length (cm) | Curl Retention (%) | Average Curl Retention (%) |
|---|---|---|---|---|
| Test A | 6.1 | 6 | 99 | 94 |
| | 6.8 | 5.9 | 89 | |
| Control A | 7.3 | 6.35 | 88 | 88 |
| | 7.3 | 6.35 | 88 | |
| Test B | 7.8 | 6.7 | 85 | 81 |
| | 7.4 | 5.4 | 77 | |
| Control B | 6.8 | 6.4 | 95 | 92 |
| | 6.8 | 6 | 90 | |

This evaluation demonstrated that compositions comprising neutralized latexes resulted in products that showed less desirable application and styling efficacy properties, e.g. poorer average curl retention, compared to compositions comprising the unneutralized form.

What is claimed is:

1. A method of styling the hair, said method comprising applying to the hair a composition comprising:
   (a) latex acrylate polymer A having a Young's modulus ranging from about 0.1 MPa to about 10 MPa, and a strain, under stress at 0.5 MPa, of at least about 1%, wherein latex acrylate Polymer A is chosen from Acrylates copolymer, Acrylates/Ethylhexyl Acrylate copolymer, or Acrylates/VA copolymer; and
   (b) latex acrylate polymer B having a Young's modulus ranging from about 10 MPa to about 6 GPa, and a strain, under stress at 0.5 MPa, of less than about 5%, wherein latex acrylate Polymer B is chosen from Acrylates copolymer, Polyacrylate-2 crosspolymer, or Styrene/Acrylic copolymer;
   wherein the total combined amount of latex polymers A and B ranges from about 0.1% to about 30% by weight, relative to the weight of the composition;
   wherein the weight ratio of latex acrylate polymers A:B ranges from about 10:1 to about 1:1 on a dry weight basis; and
   wherein said composition is in a non-aerosol form chosen from a cream, a foam, a lotion, an emulsion, or a liquid.

2. The method of claim 1, further comprising a step of treating the hair with heat at a temperature ranging from about 25° C. to about 250° C. before, during, or after the application of said composition.

3. A method of styling the hair, said method comprising applying to the hair a composition comprising:
   (1) an aqueous dispersion comprising:
      (a) latex acrylate polymer A having a Young's modulus ranging from about 0.1 MPa to about 10 MPa, and a strain, under stress at 0.5 MPa, of at least about 1%, wherein latex acrylate Polymer A is chosen from Acrylates copolymer, Acrylates/Ethylhexyl Acrylate copolymer, or Acrylates/VA copolymer; and
      (b) latex acrylate polymer B having a Young's modulus ranging from about 10 MPa to about 6 GPa, and a strain, under stress at 0.5 MPa, of less than about 5%, wherein latex acrylate Polymer B is chosen from Acrylates copolymer, Polyacrylate-2 crosspolymer, or Styrene/Acrylic copolymer; and
   (2) at least one solvent;
   wherein the total combined amount of latex polymers A and B ranges from about 0.1% to about 10% by weight, relative to the weight of the composition;
   wherein the weight ratio of latex acrylate polymers A:B ranges from about 10:1 to about 1:1 on a dry weight basis; and
   wherein said composition is in a non-aerosol form chosen from a cream, a foam, a lotion, an emulsion, or a liquid.

4. The method of claim 3, further comprising a step of treating the hair with heat at a temperature ranging from about 25° C. to about 250° C. before, during, or after the application of said composition.

5. The method according to claim 1, wherein the latex acrylate polymers A and B are, independently or together, dispersed particles in an aqueous dispersion medium.

6. The method according to claim 1, wherein the latex acrylate polymers A and B are present in a combined amount ranging from about 0.5% to about 10% by weight, relative to the weight of the composition.

7. The method according to claim 1, wherein each of the latex acrylate polymers A and B is present in individual amounts ranging from about 0.05% to about 10% by weight, relative to the weight of the composition.

8. The method according to claim 1, wherein each of the latex acrylate polymers A and B is present in individual amounts ranging from about 1% to about 15% by weight, relative to the weight of the composition.

9. The method according to claim 1, wherein the weight ratio of latex acrylate polymers A:B ranges from about 5:1 to about 1:1 on a dry weight basis.

10. The method according to claim 1, wherein the weight ratio of latex acrylate polymers A:B ranges from about 3:1 to about 1:1 on a dry weight basis.

11. The method according to claim 1, wherein the weight ratio of latex acrylate polymers A:B ranges from about 10:1 to about 3:1 on a dry weight basis.

12. The method according to claim 1, wherein the weight ratio of latex acrylate polymers A:B ranges from about 10:1 to about 5:1 on a dry weight basis.

13. The method according to claim 3, wherein latex acrylate polymers A and B are present in a combined amount ranging from about 0.5% to about 10% by weight, relative to the weight of the composition.

14. The method according to claim 3, wherein each of latex acrylate polymers A and B is present in individual amounts ranging from about 0.05% to about 10% by weight, relative to the weight of the composition.

15. The method according to claim 3, wherein latex acrylate polymers A and B are present in a combined amount up to about 8% by weight, relative to the weight of the composition.

16. The method according to claim 3, wherein weight ratio of latex acrylate polymers A:B ranges from about 5:1 to about 1:1 on a dry weight basis.

17. The method according to claim 3, wherein the weight ratio of latex acrylate polymers A:B ranges from about 3:1 to about 1:1 on a dry weight basis.

18. The method according to claim 3, wherein the weight ratio of latex acrylate polymers A:B ranges from about 10:1 to about 3:1 on a dry weight basis.

19. The method according to claim 3, wherein the weight ratio of latex acrylate polymers A:B ranges from about 10:1 to about 5:1 on a dry weight basis.

* * * * *